United States Patent [19]
Eibl et al.

[11] Patent Number: 5,608,038
[45] Date of Patent: Mar. 4, 1997

[54] HIGHLY CONCENTRATED IMMUNOGLOBULIN PREPARATION AND METHOD FOR ITS PRODUCTION

[75] Inventors: Johann Eibl; Yendra Linnau; Wolfgang Teschner, all of Vienna, Austria

[73] Assignee: Immuno Aktiengesellschaft, Vienna, Austria

[21] Appl. No.: 359,901

[22] Filed: Dec. 20, 1994

[30] Foreign Application Priority Data

Dec. 28, 1993 [DE] Germany .......................... 43 44 824.0

[51] Int. Cl.$^6$ .......................... C07K 16/00; A61K 39/395
[52] U.S. Cl. .................................. 530/387.1; 530/389.1; 424/130.1
[58] Field of Search .............................. 530/387.1, 389.1; 424/130.1

[56] References Cited

U.S. PATENT DOCUMENTS

| | | | |
|---|---|---|---|
| 4,075,193 | 2/1978 | Campbell et al. | 260/112 |
| 4,276,283 | 6/1981 | Eibl et al. | 424/130.1 |
| 4,379,086 | 4/1983 | Kimura et al. | 424/130.1 |
| 4,499,073 | 2/1985 | Tenold | 424/130.1 |
| 5,122,373 | 6/1992 | Eibl et al. | 424/130.1 |
| 5,248,767 | 9/1993 | Müller et al. | 530/387.1 |

FOREIGN PATENT DOCUMENTS

| | | |
|---|---|---|
| 3221448C2 | 3/1983 | European Pat. Off. . |
| 0122909A1 | 10/1984 | European Pat. Off. . |
| 3619565A1 | 12/1987 | European Pat. Off. . |
| 0168506 | 12/1990 | European Pat. Off. . |

OTHER PUBLICATIONS

Endobulin, Functionally Intact Immunoglobulin G For Intravenous Administration Aggregate Free, Virus Inactivated, Immuno AG (Feb. 1988).

Schiff et al., *Rapid Infusion of Sandoglobulin in Patients with Primary Humoral Immunodeficiency*, J. Allergy Clin. Immunol., 1991, vol. 88, pp. 61–67.

Herrera et al., *Immunoglobulin Composition of Three Commercially Available Intravenous Immunoglobulin Preparations*, J. Allergy Clin. Immunol., 1989, vol. 84, pp. 556–561.

*Primary Examiner*—Frank C. Eisenschenk
*Attorney, Agent, or Firm*—Foley & Lardner

[57] ABSTRACT

A stable, highly concentrated intravenously tolerable immunoglobulin preparation is described having an immunoglobulin content from 13.5 to 17.5% (w/v), an osmolarity from 250 to 600 mOs/l and a viscosity of no more than 9 cP. The immunoglobulin preparation possesses an exceptional imperishability and also is used as a highly concentrated preparation without problems due to its low viscosity.

19 Claims, No Drawings

HIGHLY CONCENTRATED IMMUNOGLOBULIN PREPARATION AND METHOD FOR ITS PRODUCTION

The invention relates to a stable, highly concentrated, intravenously tolerable immunoglobulin preparation.

BACKGROUND OF THE INVENTION

Immunoglobulins are administered to patients for the treatment of a number of infectious and immuno-regulatory disease states. The care of the patient is possible through intravenous administration with a sufficient amount of immunoglobulin. Thereby, the use of preparations with a maximal concentration of 5% or 6% is common. However, with respect to the high reliability of the infusion, highly concentrated preparations are desirable. The infusion time could be substantially shortened by the use of smaller volumes.

R. I. Schiff et al., J. Allergy Clin. Immunol., 88, 1991, 61–67, describes a lyophilised preparation which was reconstituted to a 3, 6, 9 and 12% solution. It was found that the osmolarity of the solution was very high. For example, a 12% solution had an osmolarity of 1074 mOs/l. Simultaneously, it was observed that the viscosity of the preparation was also very high. A 12% solution could hardly be administered to children in a reasonable time without difficulties. It was stated that concentrations of more than 12% are too viscous for routine use.

The osmolarity of an isotonic solution, i.e. a solution possessing the same osmotic pressure as human blood, amounts to about 300 mOs/l. In order to guarantee a good tolerance of an intravenously administrable preparation, it is desirable therefore that this has an osmolarity of less than 1000 mOs/l, and, ideally, an value corresponding to isotonicity.

Furthermore, the occurrence of IgG aggregates must be prevented in the intravenously tolerable immunoglobulin preparations. These aggregates lead namely to an undesirable anti-complimentary activity and therewith are associated with a number of side effects. Therefore, attention is paid in the formulation of a preparation that it is produced by a process which includes the removal of aggregates of this type and/or the prevention of aggregate formation. After formulation of the preparation, it is preserved preferentially through lyophilisation. However, A. M. Herrera et al., J. Allergy Clin. Immunol., 84, 1989, 556–561, suspected that aggregate formation results again through the lyophilisation of the immunoglobulin preparations.

SUMMARY OF THE INVENTION

The object of the present invention is to provide a stable immunoglobulin preparation with which the above mentioned disadvantages can be considerably overcome, and that can be administered in a highly concentrated form.

This task is solved with the subject matter of the present invention.

The subject matter of the invention relates to a stable, highly concentrated, intravenously tolerable immunoglobulin preparation.

Suitable embodiments thereof are the subject matter of the of the invention are disclosed herein.

Further subject matter of the invention is a method for the production of a stable, highly concentrated, intravenously tolerable immunoglobulin preparation.

Suitable embodiments of this method are the subject matter of the invention are disclosed herein.

DETAILED DESCRIPTION OF PREFERRED EMBODIMENTS

The immunoglobulin preparation according to the invention has an immunoglobulin content from 13.5 to 17.5% (weight/volume), and preferably from 14 to 16% (weight/volume), and possesses an osmolarity in the range from 250 to 600 mOs/l and a viscosity of not more than 9 cP, preferably from 3–8 cP.

Surprisingly, it has turned out that, despite reduction of the osmolarity, the production of a stable, highly concentrated immunoglobulin preparation is possible without having to accept the disadvantage of high viscosity. The preparation according to the invention can be quickly administered to patients due to its low viscosity, which above all is of great importance in children with narrow veins.

Preferably, the immunoglobulin preparation possesses a pH value in the range of 4 to 8. For the adjustment of the pH value, it is suitable that the formulation of the preparation according to the invention contains a buffer with a pH value in the neutral range or also in the weakly acidic range.

The immunoglobulins are advantageously contained in the preparation according to the invention in the native form, i.e. in the form of immunoglobulins which are neither fragmented nor chemically modified. Preferably, immunoglobulins are employed which essentially consist of IgG or which have a high content of IgG.

The osmolarity of the preparation can be influenced or adjusted above all through a content of carbohydrates, especially saccharides such as glucose and sucrose, of glycine and/or sodium chloride. In addition, the carbohydrates also possess a stabiliser function.

Therefore, the immunoglobulin preparation according to the invention suitably contains a content of saccharides for the stabilisation and/or adjustment of its physical parameters, particularly such as the osmolarity of the preparation formulation. In addition, the content of saccharides is preferably selected such that the osmolarity is held as low as possible in the range according to the invention of 250 to 600 mOs/l, and ideally, has the osmolarity of an isotonic solution, hence about 300 mOs/l. Moreover, the content of saccharides, as for example of glucose or sucrose, preferably lies in the range from 30 to 50 g/l. It was not to be expected that, in a highly concentrated immunoglobulin preparation with an immunoglobulin content from 13.5 to 17.5% (weight/volume), a low content of stabilisers of this type, such as for example of saccharides, corresponding to the low osmolarity suffices in order to sufficiently stabilise the immunoglobulin preparation with a content of native immunoglobulin and in a liquid state. However, through this low content of stabilisers it is possible to provide immunoglobulin preparations with the desired low viscosity.

For the adjustment of the preferred content of stabilisers, especially of saccharides, either the corresponding amount of these substances are added to the immunoglobulin preparation or are removed from the preparation employed as a starting material if this already contains a higher content of stabilisers such as for example saccharides.

The immunoglobulin preparation according to the invention can be present as a liquid preparation, in a deep-frozen form, or in lyophilised form. If proceeding from an immunoglobulin-containing fraction as a starting material which is free from IgG aggregates, the preparation can suitably be subjected to a lyophilisation for the further preservation without substantially increasing the anti-complementary activity in the preparation.

In a preferred embodiment, the immunoglobulin preparation according to the invention is present in a safeguarded form with respect to infectious agents transmittable through blood obtainable through a treatment for virus inactivation.

In addition, the treatment for virus inactivation is suitably carried out before the immunoglobulin preparation used as a starting material is adjusted to the immunoglobulin content and saccharide content according to the invention.

Preferably, a chemical treatment is carried out for virus inactivation, for example with ethanol at temperatures of less than 0° C. in an acid milieu. Moreover, the chemical treatment is carried out in the presence of stabilisers such as for example polyethylene glycol.

The method for the production of the immunoglobulin preparation according to the invention can be carried out in a known manner, for example by dissolving the immunoglobulin-containing starting material preferably present in lyophilised form in water for the adjustment of the corresponding immunoglobulin content, and adjusting the content of stabilisers, such as for example glycine and/or sodium chloride and especially of saccharides, through addition or through reduction, such as for example through diafiltration or dialysis, of the corresponding amounts to the values to obtain the desired osmolarity and viscosity according to the invention. Optionally, existing IgG aggregates are suitably removed in a known manner before or after this adjustment. The obtained end formulation is finally subjected to sterile filtration.

With the immunoglobulin preparations according to the invention, preparations are made available which have an exceptional stability of at least 2 years, favourably of at least 4 years.

Additionally, the preparations present in the form of liquid preparations according to the invention are extremely user friendly because they need not be reconstituted before their use.

The invention will now be explained in detail by the examples without limiting it to them.

The percentage data relates to the relationship weight/volume (w/v) when nothing else is stated.

EXAMPLES

Example 1

An immunoglobulin-containing lyophilised preparation (Endobulin®, IMMUNO AG) was dissolved in distilled water in a third of the recommended volume. The content of glucose and sodium chloride was adjusted accordingly by diafiltration and the solution was sterile filtered. The solution ready for infusion was of the following composition: 150 g/l immunoglobulin, 40 g/l glucose, 3 g/l sodium chloride. The viscosity of the solution was measured on a BROOKFIELD viscosimeter and the osmolarity on a KNAUER osmometer. The preparation possessed the following characteristics:

pH value: 7.0
viscosity: 7.6 cP
osmolarity: 365 mOs/l
Anti-complimentary Immediate value: 19.6 $CH_{50}$
activity: (determined according to the European Pharmacopoeia)

After 30 months storage at 4° C.: 20.5 $CH_{50}$
Monomers and dimers: Immediate value: over 96% (measured by means of HPLC)
After 30 months storage at 4° C.: over 95%
pure gammaglobulin: 97% (electrophoretically determined)

Example 2

6×1000 mg Sandoglobulin® (Sandoz) were dissolved in 40 ml of distilled water and dialysed against 4 l of a 0.3% NaCl solution each. To the dialysate, 40 mg/ml of sucrose were added. Subsequently, it was subjected to sterile filtration. The solution is suitable for i.v. use; it possesses the following characteristics:

pH. value: 6.9
viscosity: 7.5 cP
osmolarity: 388 mOs/l
Anti-complimentary
activity: 23.1 $CH_{50}$

We claim:

1. A stable, highly concentrated, intravenously tolerable immunoglobulin preparation, wherein the preparation has an immunoglobulin content from 13.5% to 17.5% (w/v), A stabilizer, a pH of 4–8, and osmolarity from 250 to 600 mOs/l and a viscosity of no more than 9 cP.

2. A preparation according to claim 1, wherein the immunoglobulin content amounts to 14 to 16% (w/v).

3. A preparation according to claim 1, wherein the viscosity amounts to 3 to 8 cP.

4. A preparation according to claim 1, wherein the stabilizer comprises carbohydrates.

5. A preparation according to claim 4, wherein the carbohydrate comprises glucose or sucrose.

6. A preparation according to claim 1, wherein the preparation comprises native immunoglobulins.

7. A preparation according to claim 1, wherein the preparation is lyophilized.

8. A preparation according to claim 1, wherein the preparation is in a liquid or deep-frozen form.

9. A preparation according to claim 1, wherein the preparation has been treated to inactivate infectious agents.

10. A method for the production of a stable, highly concentrated, intravenously-tolerable immunoglobulin preparation, comprising the steps of:

obtaining an immunoglobulin source; and dissolving immunoglobulins from the immunoglobulin source in solution to form an immunoglobulin preparation having (i) an immunoglobulin content of 13.5% to 17.5% (w/v), (ii) a stabilizer, (iii) an osmolarity of 250 to 600 mOs/l, (iv) a viscosity of no more than 9 cP, and (v) a pH of 4–8.

11. A method according to claim 10, wherein the immunoglobulins are IgG.

12. A method according to claim 11, further comprising the step of removing IgG aggregates.

13. A method according to claim 10, wherein the stabilizer comprises saccharides.

14. A method according to claim 13, wherein the saccharides are glucose or sucrose.

15. A method according to claim 10, further comprising the step of the treating the immunoglobulin preparation to inactivate infectious agents.

16. A method according to claim 10, further comprising the step of lyophilizing the immunoglobulin preparation.

17. A method according to claim 10, further comprising the step of freezing the immunoglobulin preparation.

18. A method according to claim 10, wherein the immunoglobulins are native immunoglobulins.

19. A preparation according to claim 4, wherein the carbohydrates are saccharides.

* * * * *